United States Patent [19]

Mason et al.

[11] Patent Number: 5,080,089
[45] Date of Patent: Jan. 14, 1992

[54] THERAPEUTIC APPARATUS APPLYING COMPRESSION AND A NONAMBIENT TEMPERATURE FLUID

[75] Inventors: Jeffrey T. Mason, Escondido; Bradley R. Mason, Olivenhain, both of Calif.

[73] Assignee: Breg, Inc., Vista, Calif.

[21] Appl. No.: 578,508

[22] Filed: Sep. 5, 1990

[51] Int. Cl.⁵ ............................................. A61H 9/00
[52] U.S. Cl. .................................. 128/24 R; 128/400; 128/402; 128/82.1; 137/565
[58] Field of Search ................... 128/68.1, 77, 82.1, 128/89 R, 384, 399, 400, 402, DIG. 20, 24 R, 24.1, 594; 417/502, 503; 137/209, 565, 563

[56] References Cited

U.S. PATENT DOCUMENTS

| | | | |
|---|---|---|---|
| 3,683,902 | 8/1972 | Artemenko et al. | 128/DIG. 20 X |
| 3,896,794 | 7/1975 | McGrath | 128/24 R |
| 3,942,518 | 3/1976 | Tenteris et al. | 128/24 R |
| 4,149,529 | 4/1979 | Copeland et al. | 128/400 X |
| 4,202,325 | 5/1980 | Villari et al. | 128/DIG. 20 |
| 4,335,726 | 6/1982 | Kolstedt | 128/400 |
| 4,338,944 | 7/1982 | Arkans | 128/402 X |
| 4,587,959 | 5/1986 | Ruderian | 128/24.1 |

FOREIGN PATENT DOCUMENTS 3605621 4/1987 United Kingdom ............. 128/24 R

Primary Examiner—Richard J. Apley
Assistant Examiner—L. Thomas
Attorney, Agent, or Firm—Nydegger * Associates

[57] ABSTRACT

A therapeutic apparatus is provided for treating a bodily injury or ailment by applying compression and a high or low temperature fluid to the injury or ailment. The apparatus has a cuff through which hot or cold water from a remote reservoir is continuously circulated under pressure when operating in one mode. When operating in the other mode, the cuff is filled with compressed air at ambient temperature and sealed.

17 Claims, 2 Drawing Sheets

THERAPEUTIC APPARATUS APPLYING COMPRESSION AND A NONAMBIENT TEMPERATURE FLUID

BACKGROUND OF THE INVENTION

1. Technical Field

The invention relates to an apparatus for treating bodily injuries and ailments and more particularly to an apparatus for treating bodily injuries and ailments by applying compression and a high or low temperature fluid to the affected area.

2. Background Information

Bodily injuries and ailments are commonly treated by applying high or low temperature and compression to the affected area of the body. The low temperature is typically applied in the form of ice or ice water which advantageously inhibits swelling in the region of the injury. High temperature is typically applied in the form of hot water or an active heating element which advantageously reduces pain and promotes healing. Compression, like low temperature, inhibits swelling and advantageously immobilizes the region of the injury to enhance healing. A number of splint devices are known in the art for simultaneously applying compression and high or low temperature fluids to injured or otherwise ailing areas of the body as evidenced by U.S. Pat. Nos. 3,548,819 to Davis et al; 3,901,225 to Sconce; and 4,706,658 to Cronin.

One disadvantage of such devices is that the low temperature fluids become warm as they remain in contact with the body during treatment. Conversely, high temperature fluids become cold over time. Thus, the effectiveness of both high and low temperature fluid treatments diminishes with time. This disadvantage can be remedied by periodically draining the fluid from the device and adding a fresh supply of high or low temperature fluid. However, exchange of fluids can be cumbersome or even harmful to perform with the device attached to the patient. Alternatively, the device can be removed from the patient to exchange the fluids, but this undesirably interrupts treatment.

As such a therapeutic treatment apparatus for bodily injuries and ailments is needed which enables continuous application of a high or low temperature material to the injury for as long a time period as desired without substantial change in the temperature of the material contacting the affected area. Furthermore, a therapeutic treatment apparatus is needed which enables continuous application of a relatively constant compressive force to the injured or ailing area of the body even when the high or low temperature material is withdrawn from the apparatus.

SUMMARY OF THE INVENTION

The present invention is an apparatus for the therapeutic treatment of bodily injuries and ailments, and particularly skeletal and tissue injuries and ailments, by either simultaneously or separately applying compression and a nonambient temperature fluid to the region of the injury or ailment. The apparatus is accordingly operated in one of two modes. In one mode, nonambient temperature fluid from a remote reservoir is continuously circulated under pressure through a cuff wrapped around the injury. In another mode, a fluid at ambient temperature is placed under pressure in the cuff and the cuff is sealed.

DESCRIPTION OF PREFERRED EMBODIMENTS

The apparatus of the present invention is described below with reference to the drawings. The primary components of the apparatus are a treatment means, a remote nonambient temperature fluid storage means, a fluid drive means and a fluid directional means.

Figure 1:
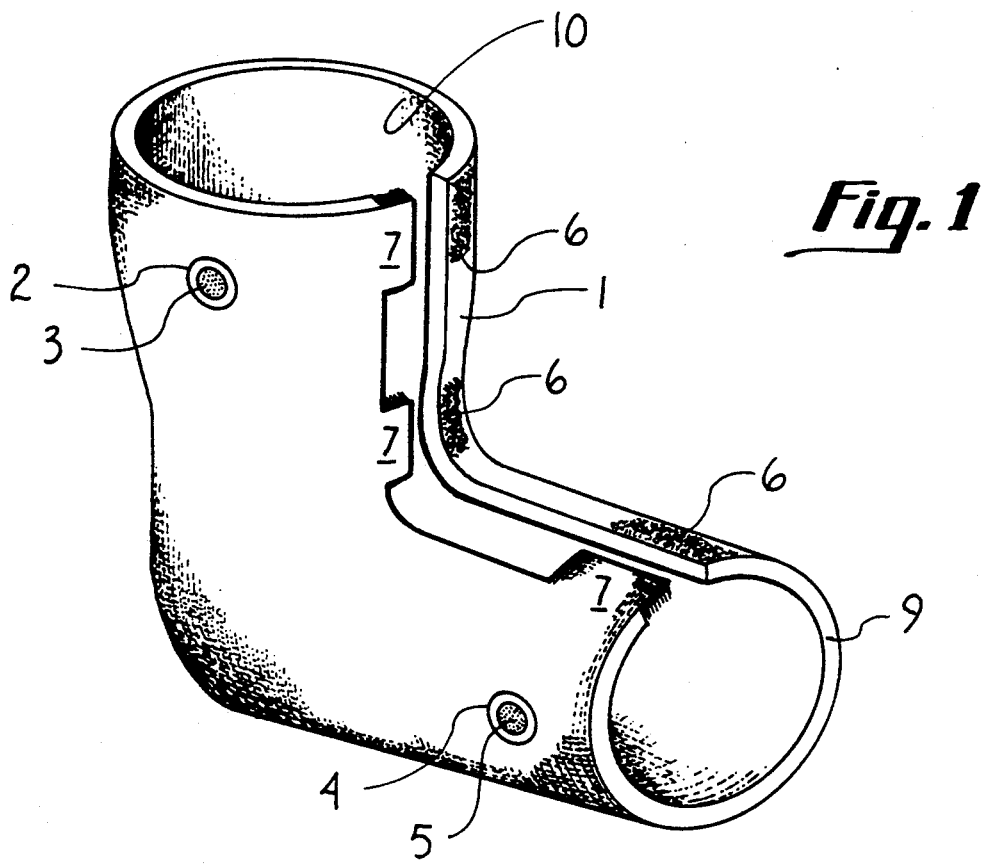
FIG. 1 is a perspective of the cuff.
Figure 2:
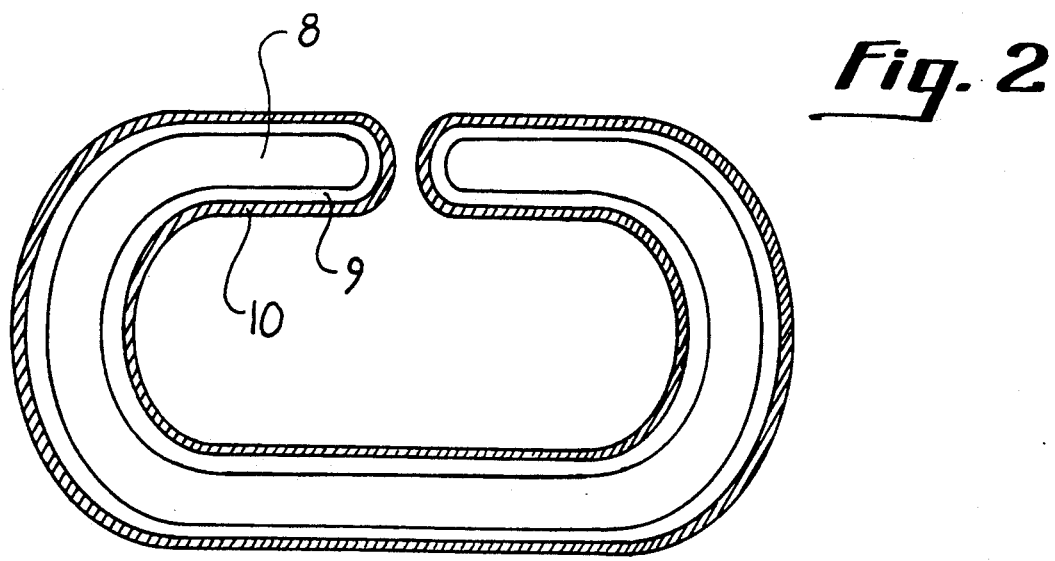
FIG. 2 is a cross-sectional view of the expanded cuff.

The preferred treatment means is a cuff as shown in FIGS. 1 and 2 having a flexible bladder 9. The skin of the bladder 9 is made from an elastomeric material capable of containing the nonambient temperature fluid. The bladder 9 has ports for receiving fluid into the bladder 9 or for withdrawing fluid from the bladder 9. In the embodiment shown, the apparatus comprises a single containment compartment 8 having two ports 2 and 4 for separate fluid inlet and outlet. Alternatively, the bladder 9 may have a plurality of separate compartments, each compartment having its own ports which enable fluids to be maintained separately within the compartments under different conditions.

The cuff 1 may be fabricated in a configuration which conforms to the particular region of the body where the treatment application is desired. In the present embodiment, the cuff 1 is configured in the form of a boot to place around the foot and ankle. Other cuff configurations are possible such as in the form of a glove to fit over the hand, or various sized sleeves to fit around an arm, a leg, or the torso.

The cuff is provided with a fastening means to enable close fitting placement around the injured or ailing body part as well as ease of removal therefrom. A preferred fastening means is one or more velcro strips 6 affixed to the cuff 1 which are positioned to engage one or more tabs 7 on opposite sides of the cuff 1 when the cuff 1 is wrapped around the injury.

The cuff 1 can further be provided with a cushioning material 10, such as a cloth or a foam, which covers the portion of the bladder contacting the injury. The cushioning material 10 can be bonded directly to the bladder 9 or can be formed as a pocket into which the bladder 9 fits. In any event, the elastomeric skin of the bladder 9 and any cushioning material 10 should be sufficiently thin so as not to excessively insulate the affected area from the high or low temperature effect of the fluid.

Figure 3:
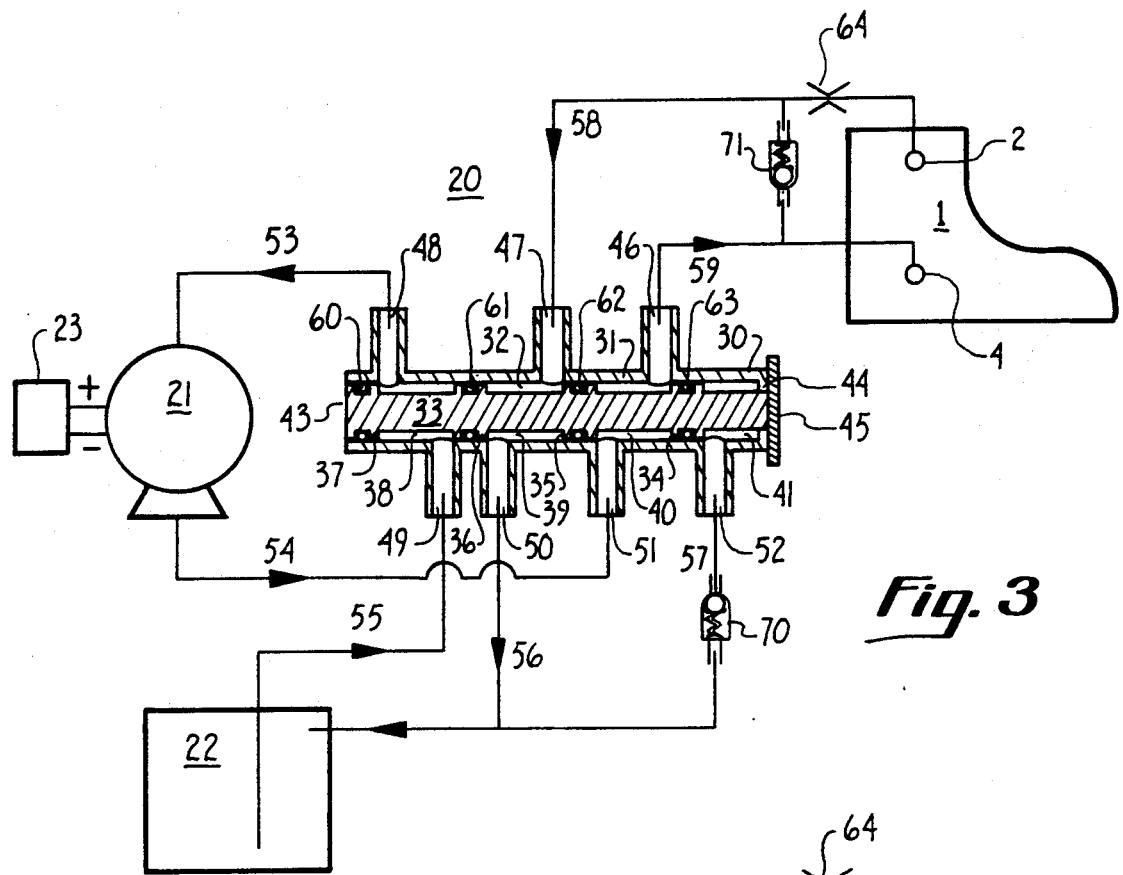
FIG. 3 is a schematic of the apparatus in the nonambient temperature fluid circulation mode of operation.
Figure 4:
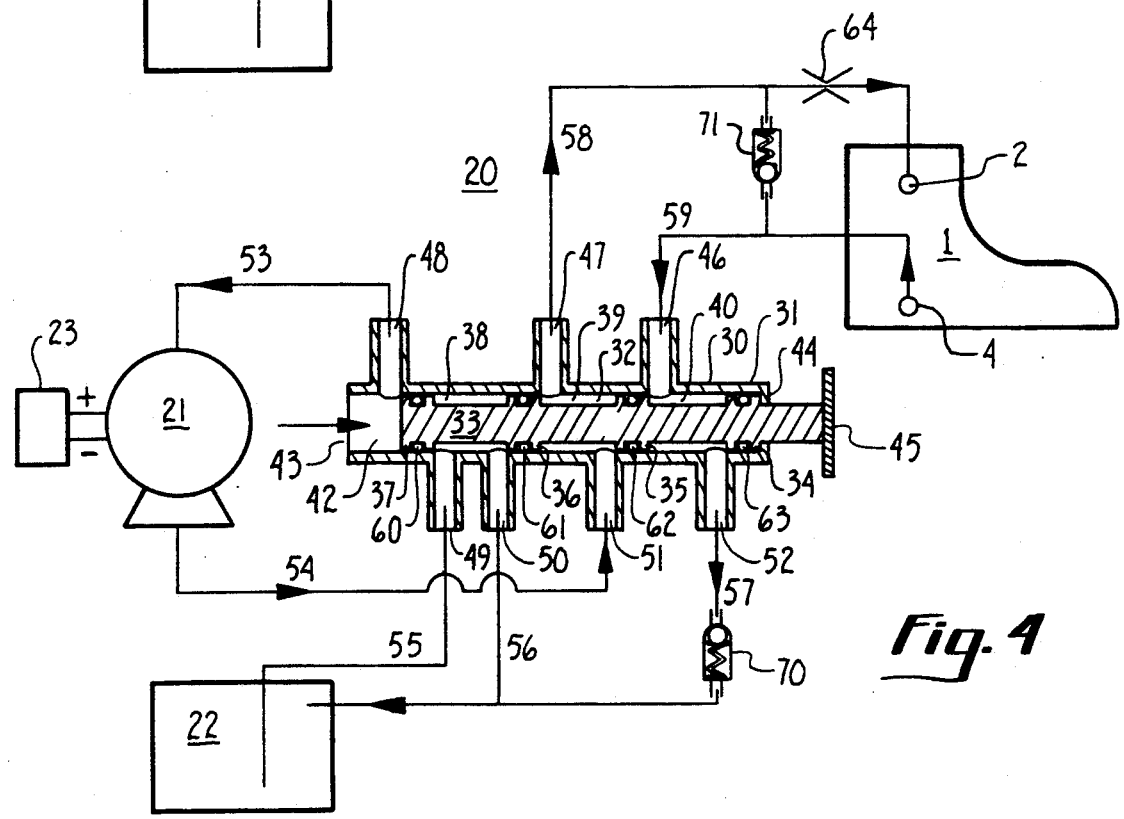
FIG. 4 is a schematic of the apparatus in the ambient temperature mode of operation.

Although shown schematically as separate in FIGS. 3 and 4, the nonambient temperature fluid storage means, fluid drive means and fluid directional means of the preferred embodiment are integrated into a single structural unit, termed the fluid circulation unit. The unit is preferably portable, i.e., capable of being hand carried by the patient should the patient desire mobility while using the apparatus, particularly in the nonambient temperature fluid circulation mode of operation.

The nonambient temperature fluid storage means is a fluid reservoir 22 having a volume which is dependent upon the volume of the bladder containment compartment 8. The preferred reservoir volume is approximately equivalent to two volumes of the expanded bladder compartment 8. The volume of the expanded bladder compartment 8 is typically on the order of 0.5 liter.

The fluid drive means comprises a power means and a pump 21 which is in fluid communication with the nonambient temperature fluid reservoir 22 and the bladder 9 via the fluid directional means. The directional means is a system 20 of plumbing lines and valves including a primary piston valve 30. The power means is preferably a battery 23 which provides electrical power to the pump 21. The pump 21 is a conventional pump such as a diaphragm pump. The pump 21 feeds fluid into or withdraws fluid out of the bladder 9 across the piston valve 30 having two positions which define the two operating modes for the apparatus.

The first operating mode is the nonambient temperature fluid circulation mode shown in FIG. 3. The arrows in the figure indicate the direction of fluid flow. Nonambient temperature fluid is defined herein as either a high temperature or a low temperature fluid which is substantially above or below the ambient temperature, i.e., room temperature.

In the first mode the piston valve 30 is positioned so that the pump withdraws nonambient temperature fluid from the reservoir 22 and feeds the fluid across the valve 30 into the bladder 9 at the desired treatment pressure. The fluid passes through the bladder 9 and back out across the valve 30 to the reservoir 22 where the fluid is heated or cooled depending on whether the treatment is high or low temperature. In this manner the nonambient temperature fluid is continuously circulated through the bladder 9 and reheated or rechilled in the reservoir 22.

The second operating mode is the ambient temperature mode shown in FIG. 4. The arrows in the figure indicate the direction of fluid flow. In this mode the piston valve 30 is positioned so that the pump 21 draws in ambient air from the atmosphere and feeds it to the bladder 9 at the desired treatment pressure. The air displaces the nonambient temperature fluid in the bladder 9 and returns it to the reservoir 22 while maintaining the bladder 9 at the desired treatment pressure. When all of the nonambient temperature fluid is removed from the bladder 9, the cuff 1 can be disconnected from the plumbing system by closing valves 3 and 5 on the inlet and outlet ports 2 and 4 of the bladder 9 to retain the compressed air at ambient temperature therein.

The piston valve 30 comprises a housing 31 enclosing a chamber 32, a piston 33 having a series of lands 34–37 and associated O-rings 60–63 which define discreet sections within the chamber 32, and a series of ports 46–52 in the housing 31 which provide communication between the chamber 32 and externally-connected fluid lines 53–59. The piston valve 30 and fluid lines 53–59 are further characterized below by a detailed operational description of the apparatus.

Operation of the apparatus in the nonambient temperature fluid circulation mode is initiated by charging the reservoir 22 with either the high or low temperature fluid. The preferred low temperature fluid is water which is chilled to a temperature range from about 0° C. to about 10° C. and preferably from about 0° C. to about 5° C.

The water can be effectively chilled by placing ice, dry ice or some other low temperature material directly in the reservoir 22 in contact with the water. Should the low temperature material be expended during operation of the apparatus, it can be readily replenished without disrupting operation of the apparatus simply by adding more of the material to the reservoir 22. Alternatively, the water can be chilled by a conventional active refrigeration system.

The preferred high temperature fluid is hot water. A preferred temperature for the hot water is in a range around 40° C. The water can be effectively heated by heating it remotely and adding it to or exchanging it with the water in the reservoir. Alternatively, the water can be heated by a conventional active heating system. Concurrent with charging the reservoir 22, the deflated cuff 1 is wrapped around the injured or ailing area of the body to be treated and fastened to provide a snug fit between the cuff 1 and the body. The piston 33 is positioned to operate in the nonambient temperature fluid circulation mode by sliding the piston 33 into the chamber 32 until the control knob 45 abuts the closed end of the housing 44. In this position lands 36 and 37 define section 38 of the chamber 32.

The pump 21 is activated and draws the nonambient water out of the reservoir through reservoir outlet line 55 and into section 38 through port 49. The nonambient water passes across section 38 and out port 48 which is connected to pump feed line 53. The pump 21 drives the nonambient water through pump outlet line 54 and port 51 which feeds into section 40 defined by lands 34 and 35. The nonambient water then passes across section 40 and out port 46 which is connected to cuff line 59. Cuff line 59 feeds the nonambient water to the bladder 9 through port 4 with valve 5 maintained in the open position.

The nonambient water flows through the bladder 9 and out port 2 with valve 3 maintained in the open position. Port 2 of the bladder 9 is connected to cuff line 58 which has a flow restriction 64 in-line. The flow restriction 64 creates a sufficient back pressure in the bladder 9 to achieve the desired pressure therein.

Cuff line 58 feeds into port 47 of the valve 30. Lands 35 and 36 define section 39 of the valve chamber 32 in fluid communication with port 50. The nonambient water is returned to the reservoir 22 across section 39 port 50 and reservoir return line 56 which is connected thereto.

The piston valve is further provided with port 52 connected to line 57 which joins into reservoir return line 56. In the first mode, port 52 is isolated from the bladder 9 by land 34 and is inoperable.

A pressure relief valve 71 is provided between cuff lines 58 and 59. The valve 71 may be a conventional spring-biased valve which opens when the water pressure in the bladder 9 exceeds a predetermined safe operating level. When the pressure relief valve 71 is in the open position, the water feed from the pump 21 bypasses the bladder 9 and goes directly back to the reservoir 22 through cuff line 58 in the manner described above.

The pump 21 is preferably operated at a fluid pressure between about 0 and about 138 kPa and preferably between about 10 and about 69 kPa. This corresponds to a continuous compressive force applied by the cuff 1 to the affected area of the body between about 20 and about 60 mm Hg.

The nonambient water is continuously circulated through the bladder 9 in the manner described above as long as the nonambient temperature treatment is desired. The preferred sequence of treating an injury or ailment using the apparatus of the present invention is to maintain continuous compression to the affected area while providing intermittent high or low temperature treatment. The high and low temperature treatments are usually limited to a finite period of time to prevent tissue damage resulting from extended exposure to nonambient temperature.

When termination of nonambient temperature treatment is desired, ambient temperature treatment is provided by repositioning the valve piston 33. The valve piston 33 is manually pulled toward the user by means of the control knob 45 until land 34 abuts the end of the piston housing 44.

In the ambient temperature mode of operation, air at ambient temperature is drawn into section 42 of the valve chamber 32 through the open end of the valve housing 43. The air is discharged out port 48 and through the pump feed line 53 into the pump 21. The air is compressed to within the above-recited pressure range by the pump 21 and fed through pump outlet line 54 back to the piston valve 30. The pump outlet line 54 feeds into the valve 30 through port 51. Lands 35 and 36 define section 39 which the compressed air passes across. The air exits port 47 and passes through cuff line 58 into the bladder 9 through port 2.

The compressed air entering the bladder displaces nonambient water from the bladder 9 via port 4 and cuff line 59. The nonambient water enters the piston valve 30 via port 46. Lands 34 and 35 direct the nonambient water across section 40 and out port 52 into line 57 joining the reservoir inlet line 56.

A pressure relief valve 70 similar to valve 71 is provided in line 57, which remains closed until line pressure reaches the threshold pressure of the valve 70, i.e., the pump operating pressure. When this pressure is reached, the valve 70 opens enabling the nonambient water to be discharged into the reservoir 22 via line 56. Ports 49 and 50 of the piston valve 30 are inoperable during the ambient temperature mode isolated from the bladder 9 by lands 36 and 37.

The pump 21 is operated in the ambient temperature mode until all of the nonambient water is displaced from the bladder 9 and the bladder 9 is filled with compressed air at ambient temperature. The bladder 9 may then be disconnected from the unit by closing valves 3 and 5 at the ports 2 and 4 of the bladder.

After disconnecting the cuff 1 from the unit, the patient can be free from the unit with the cuff in place. Whenever one desires to reinitiate nonambient temperature treatment, the unit is simply reconnected to the cuff 1 and the steps for the nonambient temperature fluid circulation mode described above are repeated.

While the foregoing preferred embodiments of the invention have been described and shown, it is understood that alternatives and modifications, such as those suggested and others, may be made thereto and fall within the scope of the invention.

We claim:

1. An apparatus for treating bodily injuries or ailments comprising:
    a bladder applied to a treatment region of the body;
    a means for circulating treatment fluids through said bladder at a pressure sufficient to apply a compression force greater than ambient atmospheric pressure to the treatment region;
    a nonambient temperature fluid reservoir in selective fluid communication with said bladder; and
    a means for selecting between said nonambient temperature fluid reservoir and an ambient temperature fluid source as a feed for circulation of said treatment fluids through said bladder.

2. The apparatus of claim 1 wherein said bladder has a treatment fluid discharge port and a treatment fluid receiving port, each port provided with a closeable valve interrupting fluid communication between said feed and said bladder when said valve is in a closed position.

3. The apparatus of claim 1 further comprising means for securing said bladder around the treatment region of the body.

4. The apparatus of claim 1 wherein said circulation means comprises a pump.

5. The apparatus of claim 2 further comprising a flow restriction on a fluid line downstream of said discharge port sufficiently restrictive to create a fluid backpressure in said bladder.

6. The apparatus of claim 1 wherein said nonambient temperature reservoir contains a liquid at nonambient temperature as a first treatment fluid and said ambient temperature source contains air at ambient temperature as a second treatment fluid.

7. The apparatus of claim 6 wherein said liquid is water at a temperature above ambient.

8. The apparatus of claim 6 wherein said liquid is water at a temperature below ambient.

9. The apparatus of claim 1 further comprising a battery powering said pump.

10. The apparatus of claim 1 wherein said bladder is shaped to conform to the treatment region of the body.

11. The apparatus of claim 6 further comprising means for heating said liquid in said reservoir.

12. The apparatus of claim 6 further comprising means for cooling said liquid in said reservoir.

13. An apparatus for treating bodily injuries or ailments comprising:
    a bladder having a receiving port for receiving treatment fluids into the interior of said bladder and a discharge port for discharging treatment fluids to the exterior of said bladder, said bladder applied to a treatment region of the body;
    a pump for circulating treatment fluids through said bladder at a pressure sufficient to apply a compression force substantially greater than ambient atmospheric pressure to the treatment region;
    a battery to power said pump;
    a nonambient temperature fluid reservoir in selective fluid communication with said bladder;
    a valve having two positions, said valve directing circulation of a first treatment fluid at a nonambient temperature from said reservoir through said bladder when in a first position and said valve directing circulation of a second treatment fluid at ambient temperature from an ambient temperature source through said bladder when in a second position; and
    a first closeable valve on said receiving port and a second closeable valve on said discharge port, said valves preventing fluid communication between the interior of said bladder and the exterior of said bladder when both are in a closed position.

14. The apparatus of claim 13 wherein said pump, battery, and nonambient temperature fluid reservoir are contained within a portable unit.

15. A method for treating a bodily injury or ailment comprising:
    applying a bladder to a treatment region of the body;
    circulating a nonambient temperature fluid through said bladder by means connected to said bladder from a nonambient temperature fluid reservoir in fluid communication with said bladder at a pressure sufficient to apply a compression force substantially greater than ambient atmospheric pressure to the treatment region;

maintaining the temperature of said nonambient temperature fluid at a nonambient level;

terminating circulation of said nonambient temperature fluid through said bladder; and displacing said nonambient temperature fluid from said bladder by feeding an ambient temperature fluid into said bladder while maintaining said compression force substantially constant.

16. The method of claim 15 further comprising sealing said bladder when said nonambient temperature fluid is completely displaced from said bladder by said ambient temperature fluid while maintaining said compression force substantially constant.

17. The method of claim 16 further comprising disconnecting said sealed bladder from said circulation means while maintaining said compression force substantially constant.

* * * * *